United States Patent [19]

Sasaki

[11] Patent Number: 4,948,520

[45] Date of Patent: Aug. 14, 1990

[54] SOFTENER COMPOSITION

[75] Inventor: Hisami Sasaki, Yokohama, Japan

[73] Assignee: Lion Corporation, Tokyo, Japan

[21] Appl. No.: 91,943

[22] Filed: Sep. 1, 1987

[30] Foreign Application Priority Data

Sep. 12, 1986 [JP] Japan ............................... 61-215136

[51] Int. Cl.$^5$ ............................................ C07C 85/06

[52] U.S. Cl. ................................ 252/8.8; 252/174.21

[58] Field of Search ............................ 252/8.8, 174.21

[56] References Cited

U.S. PATENT DOCUMENTS

| | | | |
|---|---|---|---|
| 3,325,404 | 6/1967 | Cohen | 252/8.75 |
| 3,583,912 | 6/1971 | Clark | 252/8.8 |
| 3,803,137 | 4/1974 | Egan et al. | 564/291 |
| 4,098,822 | 7/1978 | Egan | 564/480 |
| 4,214,997 | 7/1980 | Morris | 252/8.8 |
| 4,260,529 | 4/1981 | Letton | 252/547 |
| 4,264,457 | 4/1981 | Beeks | 252/8.75 |
| 4,335,024 | 6/1982 | Henneman | 252/545 |
| 4,526,694 | 7/1985 | Puchta | 252/8.8 |
| 4,678,590 | 7/1987 | Nakamura | 252/8.8 |

FOREIGN PATENT DOCUMENTS

| | | |
|---|---|---|
| 984411 | 2/1976 | Canada . |
| 2248905 | 4/1974 | Fed. Rep. of Germany . |
| 55-112376 | 8/1980 | Japan . |
| 55-116877 | 9/1980 | Japan . |
| 56-73172 | 6/1981 | Japan . |
| 1390267 | 4/1975 | United Kingdom . |

OTHER PUBLICATIONS

Derwent Abstract of J55116877-A.

Derwent Abstracts of cited Japanese Applications.

*Primary Examiner*—John F. Niebling

*Assistant Examiner*—Isabelle Rodriguez

*Attorney, Agent, or Firm*—Burns, Doane, Swecker & Mathis

[57] ABSTRACT

A softener composition comprises a mixture of (A) a mono(long-chain) quaternary ammonium salt such as monotallowalkyl trimethyl ammonium chloride, (B) a di(long-chain) quaternary ammonium salt such as ditallowalkyl dimethyl ammonium chloride and (C) a tri(-long-chain) quaternary ammonium salt such as tritallowalkyl monomethyl ammonium chloride), the weight ratio of the components (A):(B):(C) falling within the range of from 2 to 30: 96 to 50: 2 to 20, and iodine value of the mixture being in the range of 35 to 100; and (D) a polyoxyethylene adducted nonionic surfactant such as polyoxyethylene octylphenyl ether ($\overline{P}=40$). The softener composition improves the softness of natural fibers without impairing the water absorption properties thereof. It also improves the softness of chemical fibers and gives them excellent antistatic property.

18 Claims, No Drawings

SOFTENER COMPOSITION

BACKGROUND OF THE INVENTION

1. Field of the Invention

The present invention relates to a softener composition which makes it possible to impart softness and antistatic properties to a variety of clothing and in particular to a softener composition capable of improving the water absorption properties of clothing without impairing softness and antistatic properties thereof.

2. Description of the Prior Art

There have been employed various kinds of softeners in order to impart softness and antistatic properties to clothing after washing. These softeners in general comprise a di(long alkyl chain) di(short alkyl chain) quaternary ammonium salt or an imidazolinium salt as a principal component. In particular, the former has widely been utilized because of its excellent softness improving ability. The compound is adsorbed onto the surface of fibers and imparts good softness thereto. However, at the same time it also imparts water repellency thereto because of its high lipophilic nature. This leads to a reduction in the rate of water absorption of the textile goods treated with a softener containing such a cationic surfactant and the decrease in the amount of absorbed water per unit time or the apparent water absorption.

Accordingly, in order to solve the above problems of the conventional softener, many attempts have been directed to the development of novel cationic surfactants having a high compatibility with water so that the apparent water absorption of textile goods is not reduced (Japanese Patent Un-examined Publication (KOKAI) Nos. 55-66546; 56-92251 and 59-30965). In addition, attempts have been made to use the di(long alkyl chain) di(short alkyl chain) quaternary ammonium salt in combination with another surfactant of high compatibility with water. For instance, it has been combined with a fatty ethanolamide polyglycol ether (Japanese Patent Un-examined Publication No. 56-20677) and with a glycerin ether (Japanese Patent Un-examined Publication No. 56-20678).

However, since novel cationic surfactants have to sufficiently be investigated on their ability to impart intended properties such as softness, antistatic properties and apparent water absorption to chemical fibers or further with respect to the influence on the human body, only a few of them have been practically employed. In this connection, there have been known Varisoft 3690 and Rewoquat W3690 (respectively manufactured and sold by Sherex Chemicals (U.S.A.) and Rewochemische Werke (West Germany)) which are methyl-1-oleylamidethyl-2-oleylimidazolinium methyl sulfate (iodine value = 80 to 90). However, if this is used alone, it cannot impart sufficient antistatic properties to chemical textile goods as will be explained below. Therefore, it should be used in combination with other cationic or nonionic softener. On the other hand, the use of the combination of di(long alkyl chain) di(short alkyl chain) quaternary ammonium salt and another surfactant of high compatibility with water makes it possible to impart an excellent softness comparable to that of the quaternary ammonium salt to textile goods, while it is difficult to surely prevent the reduction in the apparent water absorption. Thus, there has not yet been developed a softener composition practically acceptable.

Under such circumstances, the inventors of this invention conducted various studies to develop a softener composition capable of imparting not only excellent softness and antistatic properties but also sufficient water absorption properties to textile goods, which is thus of much practical usefulness, and as a result, have proposed a softener composition in which a di(long alkyl/alkenyl chain) di(short chain) quaternary ammonium salt having unsaturated bonds and a polyoxyethylene adducted type nonionic surfactant are used in combination (Japanese Patent un-examined Publication No. 61-160482). However, as a result of subsequent investigation, it has been found that this composition is effective in improving softness of natural fiber products such as cotton and in maintaining the water absorption thereof, but is incomplete in the improvement of the softness and antistatic properties of chemical textile goods.

SUMMARY OF THE INVENTION

Accordingly, it is a primary object of the present invention to provide a softener composition capable of imparting sufficient softness to natural fibers such as cotton without impairing the water absorption properties thereof as well as capable of imparting excellent softness to chemical fibers such as acrylic and polyester fibers while providing more improved antistatic effect.

The present invention was completed on the basis of the finding that the aforementioned problems associated with the conventional softener compositions can effectively be eliminated by using mono(long-chain) tri(short chain) quaternary ammonium salts and tri(long-chain) mono(short chain) quaternary ammonium salts in combination with a di(long-chain) di(short chain) quaternary ammonium salt in a specific ratio, and using them together with a specific nonionic surfactant.

The softener composition according to the present invention comprises a mixture of the following three quaternary ammonium salts: (A) a mono(long-chain) quaternary ammonium salt having the following formula (I):

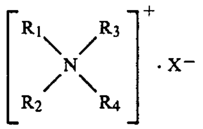

(I)

(B) a di(long-chain) quaternary ammonium salt having the following formula (II):

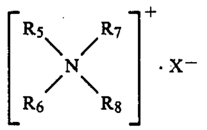

(II)

and (C) a tri(long-chain) quaternary ammonium salt having the formula (III):

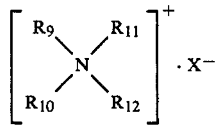

(III)

(in the general formulas (I) to (III), $R_1$, $R_5$, $R_6$, $R_9$, $R_{10}$ and $R_{11}$ may be the same or different and each represents an alkyl or an alkenyl group having 14 to 24 carbon atoms; $R_2$ represents methyl or ethyl group; $R_3$, $R_4$, $R_7$, $R_8$ and $R_{12}$ may be the same or different and each represents methyl, ethyl, polyoxyethylene or polyoxypropylene group; and X represents an anion), the weight ratio of the components, (A):(B):(C), being within the range of from 2 to 30: 96 to 50: 2 to 20, and iodine value of the mixture being in the range of 35 to 100; and (D) a polyoxyethylene adducted nonionic surfactant.

DESCRIPTION OF THE PREFERRED EMBODIMENTS

Each of the quaternary ammonium salt components (A), (B) and (C) usable in this invention is generally prepared from unsaturated higher fatty acids such as oleic acid, linoleic acid and linolenic acid; natural fatty acids such as palm oil fatty acid, soybean oil fatty acid, safflower oil fatty acid and tall oil fatty acid; or a mixture thereof; or further a mixture thereof with tallow fatty acid as the starting material. Among them, preferred are oleic acid, a mixture of oleic acid and tallow fatty acid, and palm oil fatty acid.

The foregoing quaternary ammonium salt may be obtained by subjecting these starting materials to a series of reaction processes well-known in the art, i.e., nitrification, amination to long-chain fatty amines, short-chain alkylation and quaternarization. However, the reaction conditions should strictly be selected in order to obtain quaternary ammonium salts whithout lowering the content of unsaturated bonds which lead to the reduction in the final iodine value.

$R_1$, $R_5$, $R_6$, $R_9$, $R_{10}$ and $R_{11}$ in the general formulas (I), (II) and (III) have 14 to 24, preferably 16 to 22, more preferably 16 to 18 carbon atoms and they may be identical with or different from each other. This is because if they have carbon atoms of less than 14, for instance, a mixture of quaternary ammonium salts synthesized from coconut oil fatty acid is incomplete in the ability of imparting softness to textile goods. Moreover, each of quaternary ammonium salts (I), (II) and (III) may be a mixture of comprising those having different long-chains, the number of carbon atoms of which falls within the aforesaid range.

On the other hand, $R_2$ is methyl or ethyl group and $R_3$, $R_4$, $R_7$, $R_8$ and $R_{12}$ represent a group selected from the group consisting of methyl and ethyl groups, and polyoxyethylene and polyoxypropylene groups having an average degree of polymerization of 1 to 5. Among them, preferred is methyl group. In addition, they may be identical with or different from each other.

The anion X is in general a halogen atom or a group represented by the formula: $R_{13}SO_4$. Examples of halogen atoms include chlorine, bromine and iodine and preferred is chlorine atom. $R_{13}$ is an alkyl group having 1 to 3 carbon atoms such as methyl, ethyl or propyl group.

In the softener composition of the present invention, these three kinds of quaternary ammonium salts should be mixed in a weight ratio, (A): (B): (C), of 2 to 30: 96 to 50: 2 to 20, preferably 4 to 20: 92 to 65: 4 to 15. If the component (A) is used in an amount more than the upper limit, the softening effect and the antistatic effect of the resultant composition are reduced irrespective of the kinds of fibers treated while if the component (C) is used in excess, the water absorption improving effect is lowered, which is contrary to the intended effect of the invention. More specifically, the component (C) is added to the composition to improve the softening and antistatic effects with respect to the chemical fiber products. However, if the component (B) is used in simple combination with the component (C), the water absorption improving effect of the composition is extremely lowered. For this reason, the use of the component (A) is required. Thus, it is desirable to use these components in combination for the purpose of assuring good balance between the softening, antistatic and water absorption improving effects.

In addition, the iodine value of the mixture comprising the quaternary ammonium salts should be in the range of from 35 to 100, preferably 40 to 90. This is because if it is less than 35 which is, for instance, encountered in the quaternary ammonium salt prepared from the usual tallow fatty acid inclusive of semihardened or hardened ones, hardened palm oil fatty acid, stearic acid, palmitic acid, behenic acid, or the like, the water absorption of the textile goods, in particular cotton goods, treated with such composition is substantially lowered, while it is more than 100, the softening effect and the antistatic effect with respect to chemical fabrics of the composition are lowered. In this connection, each quaternary ammonium salt per se need not have an iodine value within the foregoing range but the mixture of the ammonium salts, as a whole, must have an iodine value falling within the range. Therefore, the mixture may be obtained by combining an ammonium salt of low iodine value with one of high iodine value. The iodine value may easily be determined according to the method defined in JIS K-0070.

Referring now to the component (D), this is an essential component as a dispersion stabilizing agent when the composition is used in the form of aqueous liquid softener, alternatively as a dispersion promoting agent or a binder when the composition is used in the form of solid or granular composition.

Examples of such component (D) usable in the composition of the present invention include polyoxyethylene alkylphenyl ethers, polyoxyethylene alkyl (or alkenyl) ethers, polyoxyethylene fatty acid amides, polyoxyethylene alkyl- or alkenylamines and polyoxyethylene sorbitan fatty acid esters. Among these, preferred are POE ($\bar{P}$=10 to 70) alkyl($C_{8-12}$) phenyl ethers and/or POE ($\bar{P}$=10 to 70) alkyl (or alkenyl)($C_{10-22}$) ethers and/or POE ($\bar{P}$=10 to 70) alkyl (or alkenyl)($C_{10-22}$) amines. In these examples, POE means polyoxyethylene and $\bar{P}$ the average molar number of added ethyleneoxide (hereunder the same is also applied).

In the softener composition of the present invention, the component (D) may be incorporated into the mixture of the three quaternary ammonium salts in any proportion. However, it is desirable that the ratio, (A+B+C)/D, be in the range of 100/1 to 2/1 (weight ratio), preferably from 20/1 to 4/1.

If the softener composition of the present invention is used in the form of aqueous solution, it is desirable to use 3 to 50% by weight (hereunder simply referred to as %), preferably 4 to 30% of the mixture of the components (A), (B) and (C) and 0.02 to 20%, preferably 0.1 to 10% of the component (D). In addition, the aqueous softener composition may further comprise 1 to 20% of a hydrotrope such as ethylene glycol, propylene glycol, glycerin, urea and ethanol; a viscosity modifier such as inorganic electrolytes; and other components commonly incorporated in this kind of softener such as silicones, hydrocarbons, cellulose derivatives, antibacterial agents, pigments, dyes, perfumes and fluorescent whiteners.

Alternatively, if the softener composition of the present invention is provided in the form of solid or granular compositions, the composition comprises 3 to 50%, preferably 4 to 30% of the mixture of the three quaternary ammonium salts. In this case, the mixture consisting of the quaternary ammonium salts and the nonionic surfactant per se may be formed into granules. However, it is preferred to granulate such mixture together with other surfactants and a binder such as sodium sulfate, silica, zeolite, white carbon and water-soluble polymers. The granular softener composition thus obtained may be employed as it is and alternatively it may be used as a detergent composition having an ability of imparting softness to clothing by incorporating it into a known detergent.

Thus, according to the softener composition of the present invention, soft goods, in particular fiber products, treated with it almost completely retain their original water absorption observed before treatment and present an excellent touch. For example, the water absorption of cotton goods such as diapers substantially remains unchanged. Moreover, the softener composition of the invention simultaneously makes it possible to impart excellent softness and antistatic properties to chemical textile goods. Therefore, the composition is of high practical value.

Although, it has not yet been clarified why the softener composition of the present invention provides such excellent effects, it is assumed that these effects are attained because the three kinds of specific quaternary ammonium salts are adsorbed on the surface of fibers in a specific condition differing from that observed for each of the quaternary ammonium salts independently, while additionally the hydrophobicity thereof is compensated since at least part of these ammonium salts include unsaturated bonds in the molecules.

The softener composition of the present invention will hereunder be explained in more detail with reference to the following un-limitative working examples. Moreover, the effects practically accomplished according to the softener composition of the present invention will also be discussed in comparison with comparative examples.

In the following Examples, preparation of aqueous dispersions, softening treatment and estimation of properties were carried out according to the following.

Preparation of Aqueous Dispersion

Components other than the components (A), (B) and (C) were dissolved in water and to the resultant solution there was dropwise added a molten mixture of the components (A), (B) and (C) and isopropyl alcohol while heating the solution at 45° C. and stirring to form a uniform dispersion, followed by cooling it down to 25° C.

Finishing Treatment

Commercially available cotton towel, bleached cotton cloth, acrylic fabrics and polyester fabrics were washed two times at 50° C. in the presence of a commercially available laundry detergent for clothing with an electric washing machine and then were sufficiently washed with tap water to obtain Samples for test.

Then, a softener composition was added to 30 liters of tap water (25° C.) so that the total amount of the components (A), (B) and (C) was equal to 1 g to form a uniform solution. Each Sample was immersed in the solution thus prepared for 3 minutes at a bath ratio of 30:1 followed by draining for 2 minutes. After drying these Samples thus treated in the air, the cotton towel, bleached cotton cloth and acryl fabrics were left to stand at 25° C. and 65% RH for 24 hours to estimate the softening effect and water absorption while the acryl and polyester fabrics were left to stand at 20° C. and 55% RH for 72 hours to inspect the antistatic effect. These Samples thus treated were used in the following evaluation tests on each effect.

(i) Softness: This was estimated by comparing the touch of the cotton towel and the acryl fabrics before the treatment with that of them after treatment according to the following criteria:

+5: extremely soft
+4: very soft
+3: soft
+2: slightly soft
+1: somewhat soft
0: softness equal to that before treatment.

(ii) Water Absorption Properties: According to the method defined in JIS L1079, 5 mm of a bleached cotton cloth (2 cm×15 cm) was immersed in pure water (25° C.) colored with an ink and the height to which water rose 5 minutes was determined. In this respect, the height should be 70 mm or more from the viewpoint of acceptance criterion for softeners.

(iii) Antistatic Properties: The acryl and polyester fabrics were charged by applying a voltage of 7 KV, at a target distance of 20 mm with Static Honest Meter available from SHISHIDO Shokai Co. and the half-life (seconds) of the residual voltage after the removal of the applied voltage was measured.

EXAMPLE 1

Aqueous dispersions containing the following components were prepared and properties thereof were evaluated:

(A) mono-oleyl trimethyl ammonium chloride;
(B) dioleyl dimethyl ammonium chloride; 5%
(C) trioleyl monomethyl ammonium chloride;
(D) POE ($\bar{P}$=50) nonylphenyl ether; 0.4%
(E) sodium chloride; 0.02%
(F) ethylene glycol; 4%

(Each dispersion contained the components (A), (B) and (C) separately or in combination.)

Results are summarized in Table I. Each of the foregoing quaternary ammonium salts used is in general available as a mixture with isopropyl alcohol and, therefore, the compositions were contaminated with about 1.7% thereof.

TABLE I

| Sample No. | Quaternary Ammonium Salt (weight ratio) | Iodine Value | Water Absorption (mm) (bleached cloth) |
|---|---|---|---|
| 1(*) | A/B/C (6/90/4) | 59 | 84 |
| 2(*) | A/B/C (16/70/14) | 56 | 80 |
| 3(*) | A/B/C (30/50/20) | 55 | 78 |
| 4 | A/B/C (32/40/28) | 52 | 65 |
| 5 | B/C (60/40) | 48 | 60 |
| 6 | Only A | 70 | 95 |
| 7 | Only B | 60 | 85 |
| 8 | Only C | 20 | 58 |
| 9 | Component (*1) | 0.5 | 55 |
| 10 | — | | 100 |

| | Softness | | Antistatic | Properties (sec) |
|---|---|---|---|---|
| Sample | cotton | acryl | acryl | polyester |

TABLE I-continued

| No. | towel | jersey | jersey | jersey |
|---|---|---|---|---|
| 1(*) | +3 | +3 | 55 | 100 |
| 2(*) | +3 | +3 | 45 | 85 |
| 3(*) | +3 | +3 to +4 | 40 | 80 |
| 4 | +2 to +3 | +3 to +4 | 20 | 40 |
| 5 | +2 | +4 | 15 | 30 |
| 6 | +1 | +1 | 140 | >300 |
| 7 | +3 | +3 | 70 | 280 |
| 8 | +2 | +3 to +4 | 60 | 170 |
| 9 | +5 | +4 | 30 | 95 |
| 10 | 0 | 0 | >300 | >300 |

(*)This means the present invention.
Component (*1): di-hardened tallow dimethyl ammonium chloride used instead of the components (A), (B) and (C).

Experience shows that in order for a softener to be practically acceptable, it must produce a softness of not less than +3 and a water absorption of not less than 70 mm. In addition, the shorter the half-life, the better the antistatic properties. The results listed in Table I evidence that all of the compositions of the present invention satisfy all these requirements.

That is, the water absorption of fabrics treated with the compositions of the present invention are inferior to that of comparative Sample No. 7, but all of them satisfy the requirement for the water absorption (70 mm or more). Moreover, the compositions of the invention have a synergistic effect in that they are excellent in the improvement of softness as well as in the antistatic effect by using components (A), (B) and (C) in combination. This can be recognized from the fact that the cotton towel and the acryl jersey (typical chemical fibers) treated with the softener composition of this invention meet the foregoing requirement for softness, and for the half-life.

Furthermore, if the amount of the component (B) is insufficient (see comparative Sample No. 4), the softness and the water absorption of cotton goods become insufficient and further even if the requirements for the amount of the component (B) and the iodine value are satisfied (comparative Sample No. 5), the water absorption properties are not sufficiently improved unless the component (A) is incorporated in the composition.

The aqueous dispersions according to the present invention do not cause phase separation and/or abrupt increase in viscosity even after storage for a long period of time. It is assumed that this mainly results from the presence of the component (D) or the synergistic effect of the components (D), (E) and (F).

The quaternary ammonium salt, for instance, mono-oleyl trimethyl ammonium chloride, used in this Example is prepared from oleic acid according to a series of reaction processes known in the art and does not necessarily comprise 100% pure mono-oleyl trimethyl ammonium chloride from the chemical viewpoint. This is because at least part of the double bonds is hydrogenated during the reaction processes, in particular in the amination process and as a result the reaction product inevitably contains mono-stearyl trimethyl ammonium chloride as a by-product. The proportion of the by-product is indirectly expressed by the iodine value. The same explanation can apply to other mono-, di- or tri-long-chain alkenyl quaternary ammonium salts used in Examples 1 and 2.

EXAMPLE 2

Various kinds of mono-, di- and tri-long-chain alkyl (or alkenyl) ammonium chlorides were prepared using a variety of natural fatty acids having a different degree of unsaturation and distribution in number of carbon atoms, various aqueous dispersions having the following compositions listed in Table II were prepared therefrom and the properties thereof were estimated according in the same manner as in Example 1. The products of the present invention provide excellent results, i.e., the improvement in softness is not less than +3, water absorption of 70 mm and antistatic properties of not more than 100 seconds with respect to both cotton fiber and chemical fiber.

Moreover, as in Example 1, the aqueous dispersions of the invention were very stable and, therefore, did not cause phase separation and/or increase in viscosity even after storage for long period of time.

Each of the foregoing quaternary ammonium salts used is in general available as a mixture with isopropyl alcohol and, therefore, the compositions contained isopropyl alcohol in an amount of about ⅓ to ¼ of the total amounts of the components (A), (B) and (C).

TABLE II

| | Present Invention | | | | | Comp. Ex. | |
|---|---|---|---|---|---|---|---|
| Sample No. | 1 | 2 | 3 | 4 | 5 | 6 | 7 |
| Component A-1 | 1.4 | | | | 2.0 | | |
| Component A-2 | | 1.5 | | | | | 1.5 |
| Component A-3 | | | 1.0 | | | | |
| Component A-4 | | | | 1.0 | | | |
| Component B-1 | 10.0 | | | | | 5 | |
| Component B-2 | | 6.0 | | | | | 3.5 |
| Component B-3 | | | 3.5 | | 12.0 | | |
| Component B-4 | | | | 3.0 | | | |
| Component C-1 | 0.6 | | | | 1.0 | | |
| Component C-2 | | 0.5 | | | | | |
| Component C-3 | | | 0.5 | | | | |
| Component C-4 | | | | 1.0 | | | |
| Component D-1 | | 1.5 | | 0.5 | | | |
| Component D-2 | 2.0 | | | | 3.0 | 0.5 | |
| Component D-3 | | | 0.6 | | | | 0.5 |
| Sodium Chloride | 0.4 | 0.2 | | | | 0.01 | 0.01 |
| Ethylene Glycol | 9.0 | | 3.0 | | | | 3.5 |
| Propylene Glycol | | 6.0 | | 5.0 | | 4.0 | |
| (The balance of the deionized water) | | | | | | | |
| A/B/C (weight ratio) | 12/83/5 | 19/75/6 | 20/70/10 | 20/60/20 | 13/80/7 | | |
| Iodine Value | 35 | 39 | 83 | 48 | 75 | 35 | 41 |
| Water Absoption Properties (mm) | | | | | | | |
| Bleached Cotton | 71 | 73 | 90 | 76 | 85 | 72 | 80 |
| Softness | | | | | | | |
| cotton towel | +4 | +3 | +3 | +3 | +3 | +4 | +3 |
| acryl jersey | +3 to +4 | +3 | +3 | +4 | +3 | +2 to +3 | +2 |
| Antistatic Property (sec) | | | | | | | |
| acryl jersey | 35 | 40 | 85 | 20 | 75 | 50 | 120 |

TABLE II-continued

| | Present Invention | | | | | Comp. Ex. | |
|---|---|---|---|---|---|---|---|
| Sample No. | 1 | 2 | 3 | 4 | 5 | 6 | 7 |
| polyester jersey | 60 | 75 | 100 | 50 | 95 | 120 | 200 |

Component A-1: Monotallowalkyl Trimethyl Ammonium Chloride (iodine value-(IV) = 40; distribution in number of carbon atoms in the long-chain alkyl(Dcn) = 14 to 18)
Component A-2: Monopalmalkyl Trimethyl Ammonium Chloride (IV = 42; Dcn = 14 to 18)
Component A-3: Monotallalkyl Trimethyl Ammonium Chloride (IV = 94; Dcn = 16 to 20)Component A-4: Monodococenyl Trimethyl Ammonium Chloride (IV = 60; Dcn = 22; synthesized from cis-13-docosenic acid orginated from colza oil or the like)
Component B-1: Ditallowlkyl Dimethyl Ammonium Chloride (IV = 35)
Component B-2: Dipalmalkyl Dimethyl Ammonium Chloride (IV = 40)
Component B-3: Ditallalkyl Dimethyl Ammonium Chloride (IV = 86)
Component B-4: Didocosenyl Dimethyl Ammonium Chloride (IV = 53)
Component C-1: Tritallowalkyl Monomethyl Ammonium Chloride (IV = 15)
Component C-2: Tripalmalkyl Monomethyl Ammonium Chloride (IV = 20)
Component C-3: Tritallakyl Monomethyl Ammonium Chloride (IV = 39)
Component C-4: Tridocosenyl Monomethyl Ammonium Chloride (IV = 23)
Component D-1: POE Octylphenyl Ether ($\overline{P}$ = 40)
Component D-2: POE Tallowalkyl Amine ($\overline{P}$ = 60)
Component D-3: POE Dodecyl Ether ($\overline{P}$ = 30)

What is claimed is:

1. A softener composition comprising a mixture of the following three kinds of quaternary ammonium salts:

(A) a mono(long-chain) quaternary ammonium salt having the following formula (I):

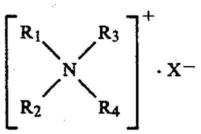
(I)

(B) a di(long-chain) quaternary ammonium salt having the following formula (II):

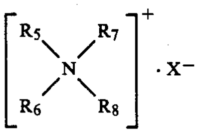
(II)

and (C) a tri(long-chain) quaternary ammonium salt having the formula (III):

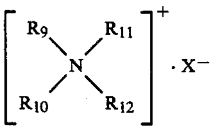
(III)

(in the formulas (I) to (III), $R_1$, $R_5$, $R_6$, $R_9$, $R_{10}$ and $R_{11}$ representing an alkyl or an alkenyl group having 14 to 24 carbon atoms; $R_2$ representing methyl or ethyl group; $R_3$, $R_4$, $R_7$, $R_8$ and $R_{12}$ representing methyl or ethyl group, or polyoxyethylene or polyoxypropylene group having an average degree of polymerization of 1 to 5; and X representing an anion), the weight ratio of the components (A):(B):(C) being within the range of from 2 to 30: 96 to 50: 2 to 20, and iodine value of the mixture being in the range of 35 to 100; and (D) a polyoxyethylene adducted nonionic surfactant.

2. A softener composition as set forth in claim 1 wherein $R_1$, $R_5$, $R_6$, $R_9$, $R_{10}$ and $R_{11}$ in the formulas (I) to (III) represent an alkyl or an alkenyl group having 16 to 22 carbon atoms.

3. A softener composition as set forth in claim 1 wherein $R_2$, $R_3$, $R_4$, $R_7$, $R_8$ and $R_{12}$ in the formulas (I) to (III) represent methyl group.

4. A softener composition as set forth in claim 1 wherein X in the formulas (I) to (III) represents a halogen atom or a group represented by the formula: $R_{13}SO_4$ in which $R_{13}$ is an alkyl group having 1 to 3 carbon atoms.

5. A softener composition as set forth in claim 4 wherein X is chlorine atom.

6. A softener composition as set forth in claim 1 wherein the weight ratio, (A):(B):(C), is 4 to 20: 92 to 65: 4 to 15.

7. A softener composition as set forth in claim 1 wherein the iodine value of the mixture of the quaternary ammonium salts is in the range of 40 to 90.

8. A softener composition as set forth in claim 1 wherein the component (D) is a member selected from the group consisting of polyoxyethylene($\overline{P}$=10 to 70) alkyl($C_8$ to C12)phenyl ethers, polyoxyethylene($\overline{P}$=10 to 70) alkyl or alkenyl ($C_{10}$ to $C_{22}$) ethers, polyoxyethylene ($\overline{P}$=10 to 70) alkyl or alkenyl($C_{10}$ to $C_{22}$) amines or a mixture thereof.

9. A softener composition as set forth in claim 1 wherein the weight ratio of the mixture of the components (A), (B) and (C) to the component (D) is 100/1 to 2/1.

10. A softener composition as set forth in claim 1 wherein the weight ratio of the mixture of the components (A), (B) and (C) to the component (D) is 20/1 to 4/1.

11. A softener composition as set forth in claim 1 wherein the composition is in the form of aqueous dispersion.

12. A softener composition as set forth in claim 11 wherein the dispersion comprises 3 to 50% by weight of the mixture of the components (A), (B) and (C) and 0.02 to 20% by weight of the component (D).

13. A softener composition as set forth in claim 11 wherein the dispersion comprises 4 to 30% by weight of the mixture of the components (A), (B) and (C) and 0.1 to 10% by weight of the component (D).

14. A softener composition as set forth in claim 12 wherein the dispersion further comprises 1 to 20% by weight of a hydrotrope selected from the group consisting of ethanol, isopropanol, ethylene glycol, propylene glycol, glycerol and mixtures thereof.

15. A softener composition as set forth in claim 1 wherein the composition is in the form of solid or granular composition.

16. A softener composition as set forth in claim 15 wherein the solid or granular composition comprises 3 to 50% by weight of the mixture of the quaternary ammonium salts.

17. A softener composition as set forth in claim 15 wherein the solid or granular composition comprises 4 to 30% by weight of the mixture of the quaternary ammonium salts.

18. A softener composition as set forth in claim 1, said composition being substantially devoid of anionic surfactant.

* * * * *